(12) United States Patent
Singh et al.

(10) Patent No.: US 7,977,376 B2
(45) Date of Patent: Jul. 12, 2011

(54) OLOPATADINE FORMULATIONS FOR TOPICAL NASAL ADMINISTRATION

(75) Inventors: Onkar N. Singh, Arlington, TX (US); G. Michael Wall, Fort Worth, TX (US); Rajni Jani, Fort Worth, TX (US); Masood A. Chowhan, Arlington, TX (US); Wesley Wehsin Han, Arlington, TX (US)

(73) Assignee: Novartis AG, Basal (CH)

( * ) Notice: Subject to any disclaimer, the term of this patent is extended or adjusted under 35 U.S.C. 154(b) by 228 days.

(21) Appl. No.: 11/703,373

(22) Filed: Feb. 7, 2007

(65) Prior Publication Data

US 2007/0142458 A1 Jun. 21, 2007

Related U.S. Application Data

(63) Continuation-in-part of application No. 11/079,996, filed on Mar. 15, 2005, now Pat. No. 7,402,609, which is a continuation of application No. 10/175,106, filed on Jun. 19, 2002, now Pat. No. 6,995,186.

(60) Provisional application No. 60/301,315, filed on Jun. 27, 2001.

(51) Int. Cl.
*A61K 31/335* (2006.01)
(52) U.S. Cl. ........................... 514/450; 424/810
(58) Field of Classification Search ........................ None
See application file for complete search history.

(56) References Cited

U.S. PATENT DOCUMENTS

| | | | | |
|---|---|---|---|---|
| 4,407,791 A | | 10/1983 | Stark | 424/80 |
| 4,749,700 A | | 6/1988 | Wenig | 514/225.2 |
| 4,778,596 A | * | 10/1988 | Linder et al. | 210/638 |
| 4,871,865 A | | 10/1989 | Lever, Jr. et al. | 549/354 |
| 4,923,892 A | | 5/1990 | Lever, Jr. et al. | 514/450 |
| 5,116,863 A | | 5/1992 | Oshima et al. | 514/450 |
| 5,164,194 A | | 11/1992 | Hettche | 424/489 |
| 5,443,833 A | * | 8/1995 | Clark et al. | 424/400 |
| 5,478,565 A | * | 12/1995 | Geria | 424/434 |
| 5,482,706 A | * | 1/1996 | Igari et al. | 424/85.7 |
| 5,641,805 A | * | 6/1997 | Hayakawa et al. | 514/450 |
| 6,054,462 A | * | 4/2000 | François et al. | 514/275 |
| 6,146,622 A | | 11/2000 | Castillo et al. | 424/78.02 |
| 6,174,914 B1 | | 1/2001 | Yanni et al. | 514/450 |
| 6,207,684 B1 | | 3/2001 | Aberg | 514/324 |

(Continued)

FOREIGN PATENT DOCUMENTS

EP  0 048 023  3/1982

(Continued)

OTHER PUBLICATIONS

PH Ratner, FC Hampel, NJ Amar, JH van Bevel, D Mohar, BF Marple, PS Roland, GM Wall, MJ Brubaker, M Drake, D Turner, LH Silver. Safety and Efficacy of Olopatadine Hydrochloride Nasal Spray for the Treatment of Seasonal Allergic Rhinitis to Mountain Cedar. Annals Allergy Asthma Immunol. 2005. vol. 95, pp. 474-479.*

(Continued)

*Primary Examiner* — Patricia A Duffy
*Assistant Examiner* — Isaac Shomer
(74) *Attorney, Agent, or Firm* — Patrick M. Ryan

(57) ABSTRACT

Topical formulations of olopatadine for treatment of allergic or inflammatory disorders of the nose are disclosed. The aqueous formulations contain approximately 0.6% (w/v) of olopatadine.

2 Claims, 4 Drawing Sheets

U.S. PATENT DOCUMENTS

| | | | |
|---|---|---|---|
| 6,316,483 B1 | 11/2001 | Hasiwanter et al. | 514/401 |
| 6,333,044 B1 | 12/2001 | Santus et al. | 424/434 |
| 6,995,186 B2 * | 2/2006 | Castillo et al. | 514/450 |
| 2001/0056093 A1 | 12/2001 | Yanni | 514/218 |
| 2006/0110328 A1 | 5/2006 | Cagle et al. | 424/45 |

FOREIGN PATENT DOCUMENTS

| | | |
|---|---|---|
| EP | 0 214 779 | 3/1987 |
| EP | 0 235 796 | 9/1987 |
| JP | 61926 | 3/1995 |
| WO | WO 00/03705 | 1/2000 |
| WO | WO 01/21209 | 3/2001 |
| WO | WO 01/21210 | 3/2001 |
| WO | WO 01/35963 | 5/2001 |
| WO | WO 01/54687 A1 | 8/2001 |
| WO | WO 02/30395 A1 | 4/2002 |
| WO | WO 03/002093 | 1/2003 |
| WO | WO 03002093 A1 * | 1/2003 |
| WO | WO 2004/043470 | 5/2004 |

OTHER PUBLICATIONS

SM Berge, LD Bighley, DC Monkhouse. "Pharmaceutical Salts." Journal of Pharmaceutical Science, vol. 66, No. 1, pp. 1-19, Jan. 1977.*

Church, "Is Inhibition of Mast Cell Mediator Release Relevant to the Clinical Activity of Anti-allergic Drugs?," *Agents and Actions*, vol. 18, ¾, pp. 288-293 (1986).

Clegg et al., "Histamine Secretion from Human Skin Slices Induced by Anti-IgE and Artificial Secretagogues and the Effects of Sodium Cromoglycate and Salbutanol," *Clin. Allergy*, vol. 15, pp. 321-328 (1985).

Hamilton et al., "Comarison of a New Antihistaminic and Antiallergic Compound KW 46790 with Terfenadine and Placebo on Skin and Nasal Provocation in Atopic Individuals," *Clinical and Experimental Allergy*, vol. 24, pp. 955-959 91994).

Ikeda et al., "Effects of Oxatomide and KW-4679 on Acetylcholine-Induced Responses in the Isolated Acini of Guinea Pig Nasal Glands," *Int. Arch. Allergy Immunol.*, vol. 106, p. 157-162 (1995).

Irani et al., "Mast Cell Heterogeneity," *Clinical and Experimental Allergy*, vol. 19, pp. 143-155 (1989).

Kamei et al., "Effects of Certain Antiallergic Drugs on Experimental Conjunctivitis in Guinea Pigs," *Atarashii Ganka*, vol. 11(4), p. 603-605 (1994) (abstract only).

Kamei et al., "Effect of (Z)-11-[3-(Dimethylamino) propylidene]-6,11-dihydrodibenz[b,e]oxepin-2-acetic Acid Hydrochloride on Experimental Allergic Conjunctivitis and Rhinitis in Rats and Guinea Pigs," *Arzneimittelforschung*, vol. 45(9), p. 1005-1008 (1995).

Ohshima et al., "Synthesis and Antiallergic Activity of 11-(Aminoalkylidene)-6,11,dihydrodibenz[b,e]oxepin Derivatives," *J. Medicinal Chemistry*, vol. 35(11), p. 2074-2084 (1992).

Pearce et al., "Effect of Disodium Cromoglycate on Antigen Evoked Histamine Release in Human Skin," *Clinical Exp. Immunol.*, vol. 17, pp. 437-440 (1974).

Pujara et al., "Effects of formulation variables on nasal epithelial cell integrity: Biochemical evaluations," *International J. of Pharmaceutics*, vol. 114, pp. 197-203 (1995).

Sharif et al., "Characterization of the Ocular Antiallergic and Antihistaminic Effects of Olopatadine (AL-4943A), a Novel Drug for Treating Ocular Allergic Diseases," *J. of Pharmacology and Experimental Therapeuticsl*, vol. 278(3), p. 1252-1261 (1996).

Sharif et al., "Olopatadine (AL-4943A): Pharmacological Profile of a Novel Anti-histaminic/Anti-allergic Drug for Use in Allergic Conjunctivitis," *Investigative Ophthalmology & Visual Science*, vol. 37(3), p. 1027 (1996) (abstract only).

Siraganian, "An Automated Continuous Flow System for the Extraction and Fluorometric Analysis of Histamine," *Anal. Biochem.*, vol. 57, pp. 383-394 (1974).

Spitalny et al., "Olopatadine Ophthalmic Solution Decreases Itching and Redness Associated with Allergic Conjunctivitis," *Investigative Ophthalmology & Visual Science*, vol. 37(3), p. 593 (1996) (abstract only).

"The Lung," *Scientific Foundation*, Raven Press, Ltd., New York, Ch. 3.4.11 (1991).

Yanni et al., "The In Vitro and In Vivo Ocular Pharmacology of Olopatadine (AL-4943A), An Effective Anti-allergic/Anti-histaminic Agent," *Investigative Ophthalmology & Visual Science*, vol. 37(3), p. 1028 (1996) (abstract only).*

Zhang et al., "Optically Active Analogues of Ebastine: Synthesis and Effect of Chirality on Their Antihistaminic and Antimuscarinic Activity," *Chirality*, vol. 6(8), p. 631-641 (1994).*

Astelin® Nasal Spray Product Insert.*

Hamilton et al., "Comarison of a New Antihistaminic and Antiallergic Compound KW 46790 with Terfenadine and Placebo on Skin and Nasal Provocation in Atopic Individuals," *Clinical and Experimental Allergy*, vol. 24, pp. 955-959, (1994).

* cited by examiner

OLOPATADINE FORMULATIONS FOR TOPICAL NASAL ADMINISTRATION

This application is a continuation-in-part of Ser. No. 11/079,996, filed Mar. 15, 2005, now U.S. Pat. No. 7,402,609 which is a continuation of Ser. No. 10/175,106, filed Jun. 19, 2002, now U.S. Pat. No. 6,995,186 which claims priority to U.S. Provisional Application Ser. No. 60/301,315, filed Jun. 27, 2001, all of which are incorporated herein by reference.

BACKGROUND OF THE INVENTION

1. Field of the Invention

The present invention relates to topical formulations used for treating allergic and inflammatory diseases. More particularly, the present invention relates to formulations of olopatadine and their use for treating and/or preventing allergic or inflammatory disorders of the nose.

2. Description of the Related Art

As taught in U.S. Pat. Nos. 4,871,865 and 4,923,892, both assigned to Burroughs Wellcome Co. ("the Burroughs Wellcome Patents"), certain carboxylic acid derivatives of doxepin, including olopatadine (chemical name: Z-11-(3-dimethylaminopropylidene)-6,11-dihydrodibenz[b,e]oxepine-2-acetic acid), have antihistamine and antiasthmatic activity. These two patents classify the carboxylic acid derivatives of doxepin as mast cell stabilizers with antihistaminic action because they are believed to inhibit the release of autacoids (i.e., histamine, serotonin, and the like) from mast cells and to inhibit directly histamine's effects on target tissues. The Burroughs Wellcome Patents teach various pharmaceutical formulations containing the carboxylic acid derivatives of doxepin, including nasal spray and ophthalmic formulations. See, for example, Col. 7, lines 7-26, and Examples 8 (H) and 8 (I) of the '865 patent.

U.S. Pat. No. 5,116,863, assigned to Kyowa Hakko Kogyo Co., Ltd., ("the Kyowa patent"), teaches that acetic acid derivatives of doxepin and, in particular, olopatadine, have anti-allergic and anti-inflammatory activity. Olopatadine is the cis form of the compound having the formula:

Medicament forms taught by the Kyowa patent for the acetic acid derivatives of doxepin include a wide range of acceptable carriers; however, only oral and injection administration forms are mentioned.

U.S. Pat. No. 5,641,805, assigned to Alcon Laboratories, Inc. and Kyowa Hakko Kogyo Co., Ltd., teaches topical ophthalmic formulations containing olopatadine for treating allergic eye diseases. According to the '805 patent, the topical formulations may be solutions, suspensions or gels. The formulations contain olopatadine, an isotonic agent, and "if required, a preservative, a buffering agent, a stabilizer, a viscous vehicle and the like." See Col. 6, lines 30-43. "[P]olyvinyl alcohol, polyvinylpyrrolidone, polyacrylic acid or the like" are mentioned as the viscous vehicle. See Col. 6, lines 55-57.

PATANOL® (olopatadine hydrochloride ophthalmic solution) 0.1% is currently the only commercially available olopatadine product for ophthalmic use. According to its labelling information, it contains olopatadine hydrochloride equivalent to 0.1% olopatadine, 0.01% benzalkonium chloride, and unspecified amounts of sodium chloride, dibasic sodium phosphate, hydrochloric acid and/or sodium hydroxide (to adjust pH) and purified water.

Topical olopatadine formulations that are effective as products for treating allergic or inflammatory conditions in the nose are desirable.

SUMMARY OF THE INVENTION

The present invention provides topical olopatadine formulations that are effective as products for treating allergic or inflammatory disorders of the nose. The formulations of the present invention are aqueous solutions that comprise approximately 0.6% olopatadine. Despite their relatively high concentration of olopatadine, they do not contain any polymeric ingredient as a physical stability enhancing ingredient. The formulations contain a phosphate salt that permits the pH of the formulations to be maintained within the range 3.5-3.95 and that also aids in solubilizing the olopatadine drug in the presence of sodium chloride.

Among other factors, the present invention is based on the finding that stable, nasal spray, solution formulations of olopatadine can be prepared within a pH range of 3.5-3.95 using a phosphate buffer without the need for any polymeric ingredient to enhance the solubility or physical stability of the formulation.

DETAILED DESCRIPTION OF THE INVENTION

Unless indicated otherwise, all component amounts are presented on a % (w/v) basis and all references to amounts of olopatadine are to olopatadine free base.

Olopatadine is a known compound that can be obtained by the methods disclosed in U.S. Pat. No. 5,116,863, the entire contents of which are hereby incorporated by reference in the present specification. The solution formulations of the present invention contain 0.54-0.62% olopatadine. Preferably, the solution formulations contain 0.6% olopatadine.

Olopatadine has both a carboxylic functional group ($pKa_1=4.18$) and a tertiary amino group ($pKa_2=9.79$). It exists in different ionic forms depending upon the pH of the solution. Olopatadine exists predominantly as a zwitterion in the pH range between the two pKa values with a negatively-charged carboxylic group and a positively-charged tertiary amino group. The iso-electric point of the olopatadine zwitterion is at pH 6.99. At a pH lower than $pKa_1$, cationic olopatadine (with ionized tertiary amino group) is dominant. At a pH higher than $pKa_2$, anionic olopatadine (with ionized carboxylic group) is dominant.

Acid-Base Equilibrium of Olopatadine

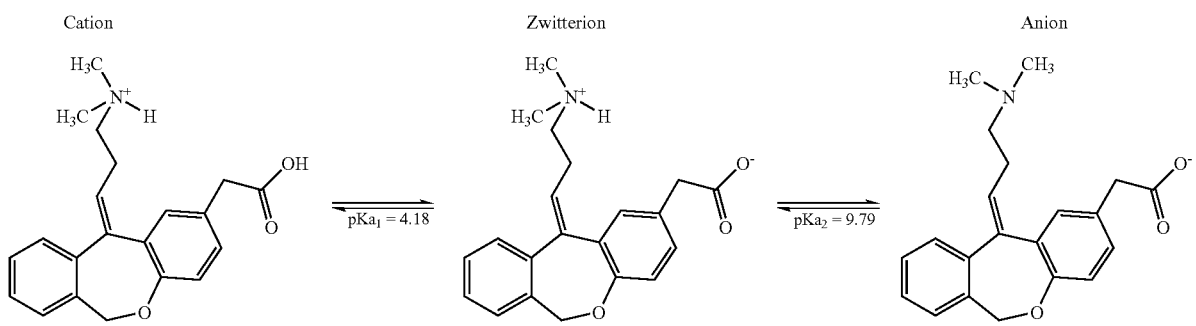

Figure 1A:
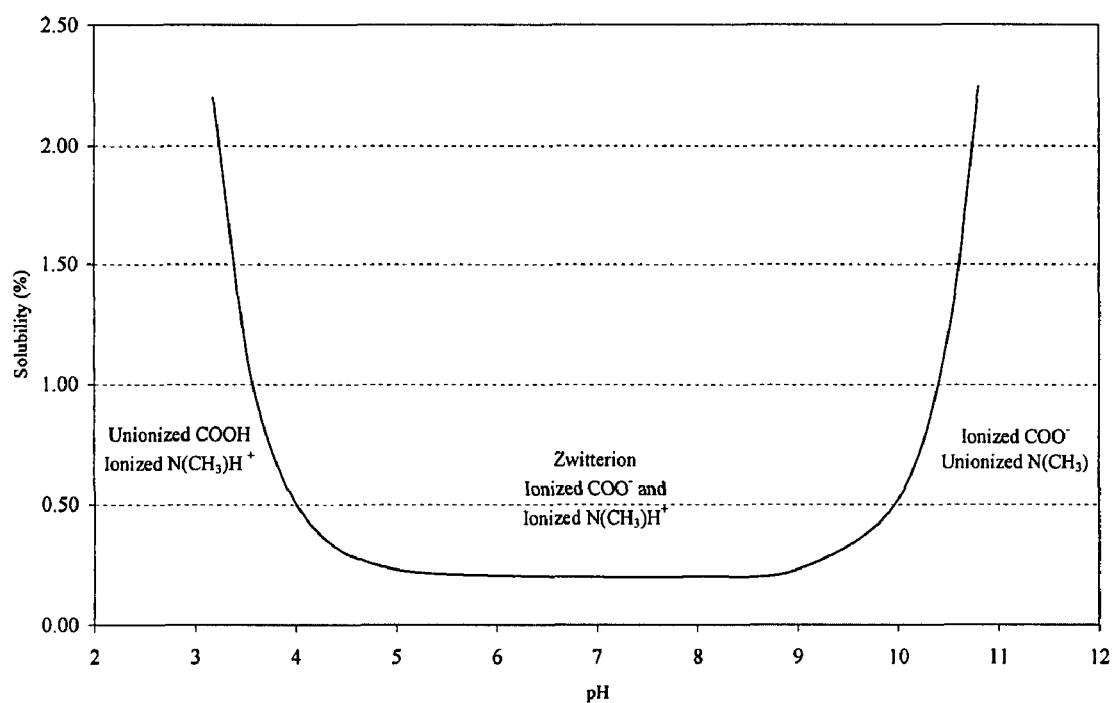
FIGS. 1A and 1B show the pH-solubility profile of olopatadine.
Figure 1B:
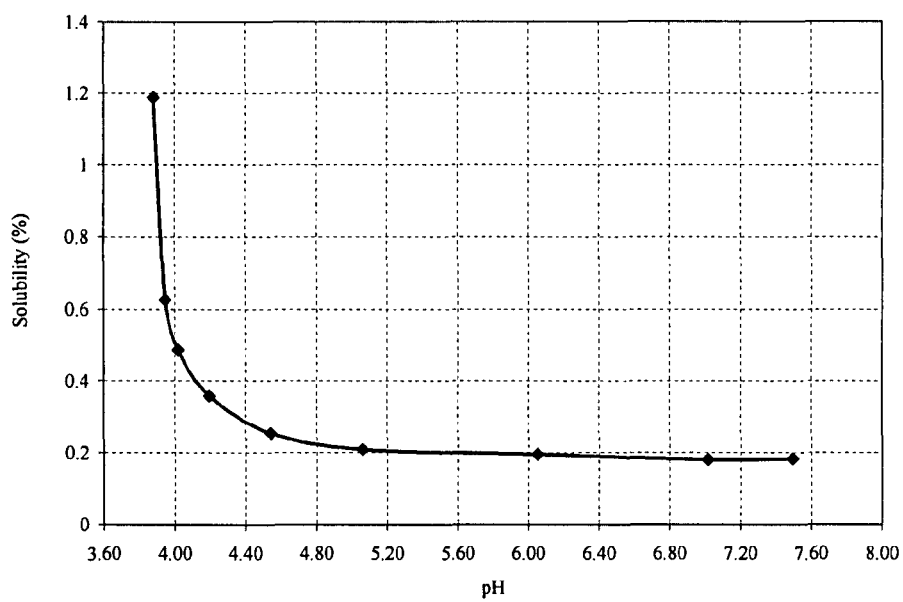

In many zwitterionic molecules, such as various amino acids, intra-molecular ionic interactions are not significant or do not exist. But the structure of olopatadine is such that intra-molecular interactions exist and are significant, possibly due to the distance and bonding angle between the oppositely charged functional groups. This interaction effectively reduces the ionic and dipole character of the molecule. The net effect of the intra-molecular interactions between the oppositely charged functional groups is the reduction of aqueous solubility of olopatadine. Olopatadine has the pH-solubility profile shown in FIGS. 1A (theoretical) and 1B (obtained using phosphate buffer).

Generally, olopatadine will be added in the form of a pharmaceutically acceptable salt. Examples of the pharmaceutically acceptable salts of olopatadine include inorganic acid salts such as hydrochloride, hydrobromide, sulfate and phosphate; organic acid salts such as acetate, maleate, fumarate, tartrate and citrate; alkali metal salts such as sodium salt and potassium salt; alkaline earth metal salts such as magnesium salt and calcium salt; metal salts such as aluminum salt and zinc salt; and organic amine addition salts such as triethylamine addition salt (also known as tromethamine), morpholine addition salt and piperidine addition salt. The most preferred form of olopatadine for use in the solution compositions of the present invention is the hydrochloride salt of (Z)-11-(3-dimethylaminopropylidene)-6,11-dihydrodibenz-[b,e]oxepin-2-acetic acid. When olopatadine is added to the compositions of the present invention in this salt form, 0.665% olopatadine hydrochloride is equivalent to 0.6% olopatadine free base. Preferably the compositions of the present invention comprise approximately 0.665% olopatadine hydrochloride.

In addition to olopatadine, the aqueous solution compositions of the present invention comprise a phosphate salt. The phosphate salt not only helps maintain the pH of the compositions within the targeted pH range of 3.5-3.95 by contributing to the buffer capacity of the compositions, but also helps solubilize olopatadine. Suitable phosphate salts for use in the compositions of the present invention include monobasic sodium phosphate, dibasic sodium phosphate, tribasic sodium phosphate, monobasic potassium phosphate, dibasic potassium phosphate, and tribasic potassium phosphate. The most preferred phosphate salt is dibasic sodium phosphate. The compositions of the present invention comprise an amount of phosphate salt equivalent (on an osmolality contribution basis) to 0.2-0.8%, preferably 0.3-0.7%, and most preferably 0.4-0.6% of dibasic sodium phosphate. In a preferred embodiment, the phosphate salt is dibasic sodium phosphate at a concentration of 0.4-0.6% (w/v). In a most preferred embodiment, the compositions contain 0.5% (w/v) dibasic sodium phosphate.

Phosphate buffer is commonly used in aqueous pharmaceutical compositions formulated near neutral pH. Phosphate buffer ($pKa_1$=2.12, $pKa_2$=7.1, $pKa_3$=12.67) would not normally be chosen for an aqueous composition with a target pH range of 3.5-3.95 because it has low buffer capacity in that region. Other buffering agents are commonly used in aqueous pharmaceutical compositions, including acetate, citrate and borate buffers, but are not suitable for use in the topical nasal compositions of the present invention. Borate buffers are not suitable because they do not have any significant buffer capacity in the pH range 3.5-3.95. Though acetate and citrate buffers have buffer capacity in this region, they are not preferred because they have the potential to cause irritation to nasal mucosal tissues and undesirable taste and/or smell.

In addition to olopatadine and phosphate salt, the compositions of the present invention comprise sodium chloride as a tonicity-adjusting agent. The compositions contain sodium chloride in an amount sufficient to cause the final composition to have a nasally acceptable osmolality, preferably 240-350 mOsm/kg. Most preferably, the amount of sodium chloride in the compositions of the present invention is an amount sufficient to cause the compositions to have an osmolality of 260-330 mOsm/kg. In a preferred embodiment, the compositions contain 0.3-0.6% sodium chloride. In a more preferred embodiment, the compositions contain 0.35-0.55% sodium chloride, and in a most preferred embodiment, the compositions contain 0.35-0.45% sodium chloride.

The compositions of the present invention also contain a pharmaceutically acceptable pH-adjusting agent. Such pH-adjusting agents are known and include, but are not limited to, hydrochloric acid (HCl) and sodium hydroxide (NaOH). The compositions of the present invention preferably contain an amount of pH-adjusting agent sufficient to obtain a composition pH of 3.5-3.95, and more preferably, a pH of 3.6-3.8.

In one embodiment, the aqueous compositions of the present invention consist essentially of olopatadine, phosphate buffer, sodium chloride, a pH-adjusting agent, and water, and have a pH from 3.5-3.95. These compositions can be manufactured as sterile compositions and packaged in multi-dose, pressurized aerosol containers to avoid microbial contamination. In another embodiment, the aqueous compositions of the present invention contain a preservative and a chelating agent such that the compositions pass United States Pharmacopeia/National Formulary XXX criteria for antimicrobial effectiveness, and more preferably the Pharm. Eur. $5^{th}$ Edition criteria for antimicrobial preservation (Pharm. Eur. B preservative effectiveness standard). Suitable preservatives include p-hydroxybenzoic acid ester, benzalkonium chloride, benzododecinium bromide, and the like. Suitable chelating agents include sodium edetate and the like. The most preferred preservative ingredient for use in the compositions of the present invention is benzalkonium chloride ("BAC"). The amount of benzalkonium chloride is preferably 0.005-0.015%, and more preferably 0.01%. The most preferred chelating agent is edetate disodium ("EDTA"). The amount of edetate disodium in the compositions of the present invention is preferably 0.005-0.015%, and more preferably 0.01%.

The aqueous solution compositions of the present invention do not contain a polymeric ingredient intended to enhance the solubility of olopatadine or the physical stability of the solution. For example, the compositions of the present invention do not contain polyvinylpyrrolidone, polystyrene sulfonic acid, polyvinyl alcohol, polyvinyl acrylic acid, hydroxypropylmethyl cellulose, sodium carboxymethyl cellulose or xanthan gum.

The compositions of the present invention are preferably packaged in opaque plastic containers. A preferred container is a high-density polyethylene container equipped with a nasal spray pump. Preferably, the package is designed to provide the spray characteristics described in commonly-assigned, co-pending, U.S. Patent Application Publication No. 2006/0110328, which is incorporated herein by reference.

The present invention also relates to a method of treating allergic rhinitis comprising topically administering to the nasal cavities a composition containing 0.6% olopatadine, phosphate buffer, sodium chloride, a pH-adjusting agent, and water. The compositions optionally contain one or more preservative ingredients. Preferably, the compositions are administered such that 1200 mcg of olopatadine (e.g., 600/mcg per 100 microliter spray×two sprays) is delivered to each nostril twice per day.

Certain embodiments of the invention are illustrated in the following examples.

Example 1

Topically Administrable Nasal Solution

TABLE 1

| Ingredient | Amount (%, w/v) |
| --- | --- |
| Olopatadine Hydrochloride | 0.665[a] |
| Benzalkonium Chloride | 0.01 |
| Edetate Disodium, Dihydrate | 0.01 |
| Sodium Chloride | 0.41 |
| Dibasic Sodium Phosphate, Anhydrous | 0.5 |
| Hydrochloric Acid and/or Sodium Hydroxide | Adjust to pH 3.7 ± 0.1 |
| Purified Water | qs to 100 |

[a]0.665% w/v olopatadine hydrochloride (665 mcg/100 microliter spray) is equivalent to 0.6% w/v olopatadine as base (600 mcg/100 microliter spray).

An exemplary compounding procedure for the nasal composition shown in Table 1 is described as below.
1. Tare a suitable compounding vessel with magnetic stir bar. Add approximately 80% of the batch weight of purified water.
2. While stirring, add dibasic sodium phosphate (anhydrous), sodium chloride, edetate disodium, benzalkonium chloride and olopatadine HCl.
3. Add equivalent to approximately 0.55 g, 6N hydrochloric acid per 100 ml batch.
4. Allow adequate time between each addition for dissolution of each ingredient
5. Add purified water to approximately 90% of final batch weight.
6. Measure pH and adjust, if necessary, to 3.7 with 6N (and/or 1N) hydrochloric acid and 1N sodium hydroxide.
7. Adjust to final batch weight with purified water (QS).
8. Measure final pH.
9. Filter through 0.2 μm filtration membrane.

Example 2

Effect of NaCl and Phosphate Buffer on Dissolution of Olopatadine Hydrochloride

Figure 2:
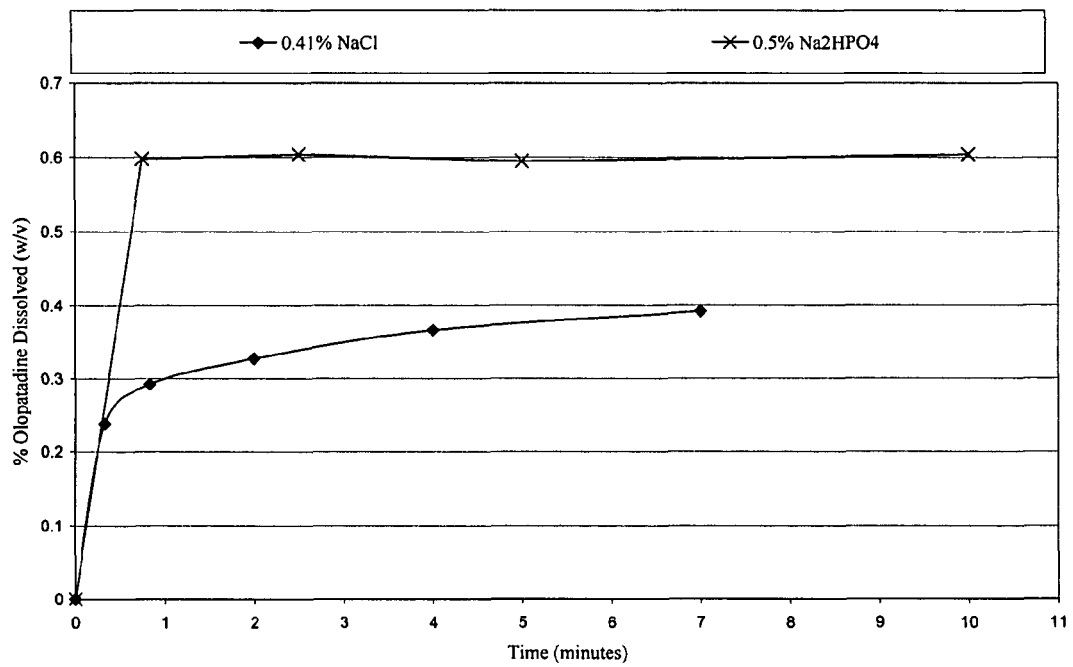
FIG. 2 shows the effect of NaCl and $Na_2HPO_4$ on the dissolution of olopatadine in water.

The effect of NaCl on the dissolution rate of olopatadine hydrochloride in water was determined. NaCl caused a significant reduction in the rate of dissolution of olopatadine. With addition of $Na_2HPO_4$, however, the dissolution of olopatadine was dramatically improved. The complete dissolution of 0.6% olopatadine solution without $Na_2HPO_4$ would take at least several hours assuming that the entire amount of olopatadine would eventually dissolve, but with $Na_2HPO_4$ it takes less than one minute. The results are shown in FIG. 2.

Example 3

Figure 3:
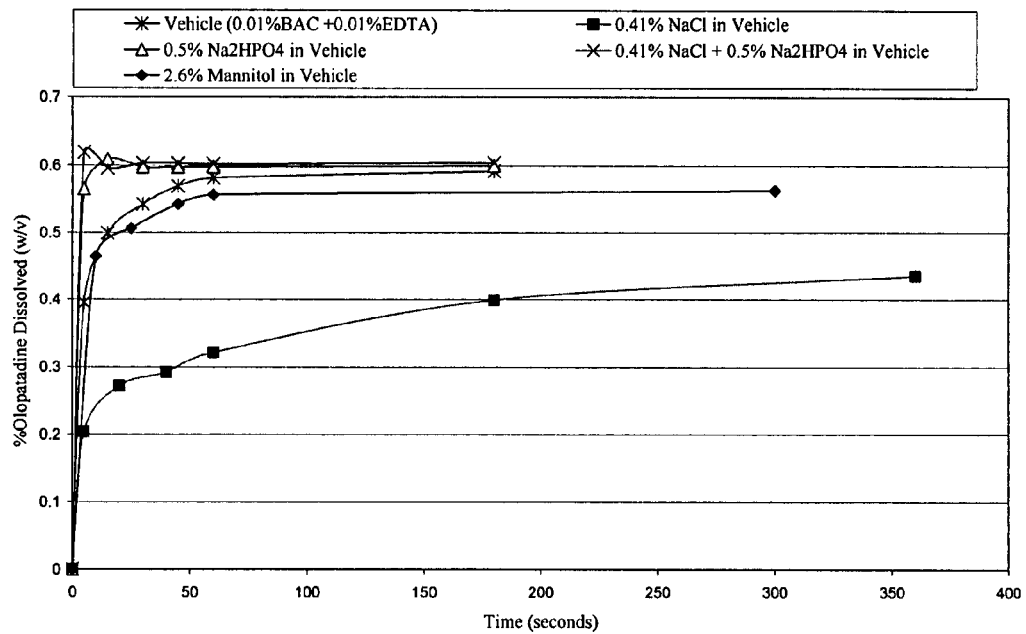
FIG. 3 shows the effect of NaCl and $Na_2HPO_4$ on the dissolution of olopatadine in a nasal vehicle.

Effect of NaCl and $Na_2HPO_4$ on the Dissolution Olopatadine Hydrochloride in a Nasal Vehicle The effect of NaCl, Na2HPO4, and mannitol on the dissolution rate of olopatadine hydrochloride in a nasal formulation containing 0.01% EDTA and 0.01% BAC was determined. The results are shown in FIG. 3. The effect of phosphate salt in this vehicle is the same as that shown in water in Example 2.

Example 4

Effect of NaCl and $Na_2HPO_4$ Concentrations on Dissolution

Figure 4:
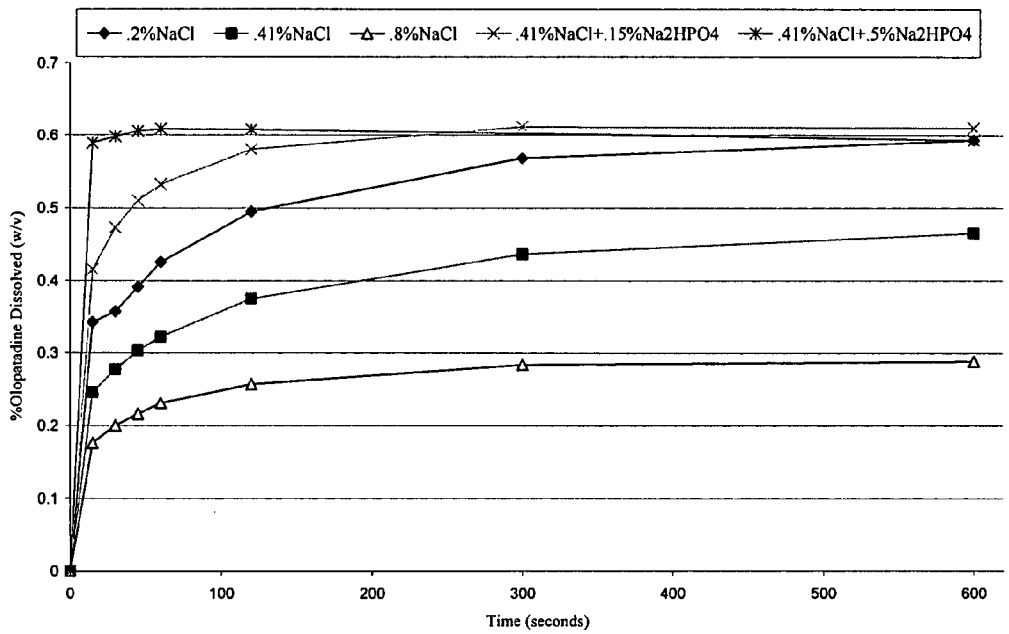
FIG. 4 shows the effect of NaCl and $Na_2HPO_4$ concentrations on the dissolution rate of olopatadine in a nasal vehicle.

The effect of NaCl and $Na_2HPO_4$ concentrations on the dissolution rate of olopatadine hydrochloride in a nasal formulation containing 0.01% EDTA and 0.01% BAC was determined. The results are shown in FIG. 4. The aqueous solubility of olopatadine HCl decreases with increasing concentration of NaCl. However, increasing phosphate buffer correlates with increased aqueous solubility of olopatadine HCl in the presence of NaCl.

Example 5

Effect of Phosphate Buffer on Olopatadine Nasal Spray Composition

The two compositions shown in Table 2 below were prepared using the procedure described in Example 1 and visual observations of the compositions clarity were made at different points during the compounding procedure. The results are shown in Table 2.

TABLE 2

| Component | Formulation 2A % w/v | Formulation 2B % w/v |
|---|---|---|
| Olopatadine HCl | 0.665 | 0.665 |
| Benzalkonium Chloride | 0.01 + 3% xs | 0.01 + 3% xs |
| Disodium EDTA | 0.01 | 0.01 |
| Sodium Chloride | 0.37 | 0.7 |
| Dibasic Sodium Phosphate | 0.5 | absent |
| Sodium Hydroxide | pH to 3.7 | pH to 3.7 |
| Hydrochloric Acid | pH to 3.7 | pH to 3.7 |
| Purified Water | qs 100 | qs 100 |
| Batch Size | 2000 mL | 2000 mL |
| Osmolality | 266 | 250 |
| Initial pH | 6.704 | 3.189 |
| Final pH | 3.699 | 3.618 |
| Visual Observations: | | |
| Upon addition of HCl | Solution appeared clear with a few particles | Solution appeared cloudy with many particles suspended |
| After overnight stirring | Solution became cloudy with many particles | Solution remained cloudy with many particles |
| Final pH adjustment | Solution began to clear during pH adjust down to 3.7 | Solution remained cloudy even after pH adjust down to 3.6 |
| Add final batch quantity of water (approximately 10%) | Solution remained clear | Solution was still cloudy with many particles |

The results for Formulation A show that it is a clear solution. The results for Formulation B show that despite the pH-solubility profile indicating 0.6% olopatadine should dissolve at pH 3.189, the olopatadine did not go into solution. These results demonstrate that, without phosphate buffer, 0.665% olopatadine hydrochloride did not completely dissolve in water in the presence of 0.7% NaCl at a pH as low as 3.6 using the compounding procedure described in Example 1.

Example 6

Effect of Phosphate Buffer Added to Cloudy 0.6% Olopatadine Nasal Spray Composition Formulations 3A, 3B, and 3C shown in Table 3 were prepared without phosphate buffer and, despite extensive stirring, the olopatadine HCl was not completely solubilized. A portion of Formulation 3C was removed and phosphate buffer was added to form Formulation 3D. The results, summarized in Table 3, demonstrate that 0.665% olopatadine hydrochloride is not soluble in the tested nasal vehicle without a phosphate salt.

TABLE 3

| | Formulation 3A | Formulation 3B | Formulation 3C | Formulation 3D |
|---|---|---|---|---|
| Olopatadine HCl | 0.665 | 0.665 | 0.665 | 0.665 |
| Benzalkonium Chloride | 0.01 + 3% xs | 0.01 + 3% xs | 0.01 + 3% xs | 0.01 + 3% xs |
| Disodium EDTA | 0.01 | 0.01 | 0.01 | 0.01 |
| Sodium Chloride | 0.33 | 0.7 | 0.7 | 0.7 |
| Sodium Hydroxide | pH to 3.7 | pH to 3.7 | pH to 3.7 | pH to 3.7 |
| Hydrochloric Acid | pH to 3.7 | pH to 3.7 | pH to 3.7 | pH to 3.7 |
| Purified Water | qs 100% | qs 100% | qs 100% | qs 100% |
| Batch Size | 300 mL | 800 mL | 2000 mL | 100 mL |
| Osmolality | 137 | 246 | 250 | — |
| Initial pH | 3.002 | 3.176 | 3.189 | 6.908 |

TABLE 3-continued

|  | Formulation 3A | Formulation 3B | Formulation 3C | Formulation 3D |
|---|---|---|---|---|
| Final pH | 3.002 | 3.664 | 3.618 | 3.7 |
| Visual Observations: | Upon addition of Olopatadine HCl, solution appeared cloudy, batch was qs to 100% and still cloudy | Upon addition of Olopatadine HCl, solution appeared cloudy, batch was qs to 90% and pH adjusted, solution still cloudy | Upon addition of Olopatadine HCl, solution appeared cloudy | Used dibasic sodium phosphate (0.5%) in attempts to clarify a portion of the cloudy solution (Formulation 3C) |
|  | After 2.5 hours of stirring, solution began to clear but still many particles* in solution | After 7 hours of stirring, the solution was still cloudy. | After overnight stirring, the solution remained cloudy with many particles* | Within a minute of stirring, the solution became clear with a few particles** in solution (mostly fibrous in appearance) |
|  | After 3.5 hours of stirring, solution appeared clear with particles* | After 7 days of stirring, the solution was still cloudy with many particles* | After final qs to 100% and pH adjust, the solution was still cloudy with many particles* | After qs to 100% (using solution from the original batch), the solution remained clear with a few fibrous particles** |
|  | After overnight stirring, solution appeared clear with several particles* | The batch was qs to 100% and still cloudy with many particles* | After approx. 7 hours of stirring, the solution was cloudy with many particles* |  |

*Insoluble drug related
**Extraneous fibrous particles

Example 7

Effect of Compounding Sequence on 0.6% Olopatadine Nasal Spray Composition

The composition of Example 1 above was prepared using four different sequences for the addition of ingredients. The four sequences are indicated in Table 4 in the "OA" (order of addition) columns. In each case, visual observations relating to the composition's clarity were recorded. The results are shown in Table 4. In all four cases (Formulations 4A-4D), at the end of the compounding procedure, the solutions were clear. (The solutions contained some extraneous fibrous particles that did not appear to be related to the drug or the formulation excipients and were likely attributable to laboratory equipment and glassware.)

TABLE 4

|  | 4A | | 4B | | 4C | | 4D | |
|---|---|---|---|---|---|---|---|---|
| Component | % w/v | OA[a] | % w/v | OA[a,c] | % w/v | OA[a] | % w/v | OA[a] |
| Olopatadine HCl | 0.665 | 3 | 0.665 | 5 | 0.665 | 2 | 0.665 | 2 |
| Benzalkonium Chloride | 0.01 | 4 | 0.01 | 4 | 0.01 | 3 | 0.01 | 4 |
| Disodium EDTA | 0.01 | 5 | 0.01 | 3 | 0.01 | 4 | 0.01 | 5 |
| Sodium Chloride | 0.41 | 6 | 0.41 | 2 | 0.41 | 5 | 0.41 | 6 |
| Dibasic Sodium Phosphate (Anhydrous) | 0.5 | 1 | 0.5 | 1 | 0.5 | 6 | 0.5 | 1 |
| Sodium Hydroxide | pH to 3.7 | NA[b] | pH to 3.7 | NA[b] | pH to 3.7 | NA[b] | pH to 3.7 | NA[b] |
| Hydrochloric Acid | pH to 3.7 | 2 | pH to 3.7 | 6 | pH to 3.7 | 1 | pH to 3.7 | 3 |
| Purified Water | qs 100% | NA | qs 100% | NA | qs 100% | NA | qs 100% | NA |
| Batch Size | 100 mL | | 100 mL | | 100 mL | | 100 mL | |
| Sodium Hydroxide added | 0.238 g (1N) | | None | | None | | None | |
| Hydrochloric Acid added | 0.576 g (6N) | | 0.550 g (6N) | | 0.550 g (6N) | | 0.550 g (6N) | |
| Initial Observations | Cloudy, many suspended particles | | Cloudy, many suspended particles | | Cloudy, many suspended particles | | Cloudy, many suspended particles | |
| Additional observations | After 10 minutes - solution began to clear, many suspended particles | | After 1 minute - clear with several suspended particles | | After 2 minutes - clear with a few suspended particles | | After 5 minutes - clear with a few suspended particles | |
|  | After 30 minutes - clear with several suspended particles | | After 6 minutes - clear with a few suspended particles | | After 7 minutes - clear with a few suspended particles | | After 20 minutes - clear with a few suspended particles | |
|  | After 1 hour - clear with many suspended particles* | | After 1 hour - clear with a few suspended particles* | | After 1 hour - clear with several suspended particles* | | After 1 hour - clear with several suspended particles* | |
|  | Next day (approx 16 hours) - clear with several particles* | | Next day (approx 16 hours) - clear with a few particles* | | Next day (approx 16 hours) - clear with a few particles* | | Next day (approx 16 hours) - clear with a few particles* | |
| pH | 3.698 | | 3.692 | | 3.718 | | 3.724 | |
| Osmolality | 274 | | 283 | | 279 | | 280 | |

[b]NA = not applicable
[c]Preferred method of manufacturing
*Extraneous fibrous particles

Example 8

Effect of Various Buffer Systems

The composition of Example 1 above was prepared but acetate, borate and citrate buffers, respectively, were substituted in place of the phosphate buffer. Visual observations regarding the clarity of each of the compositions were recorded and are shown in Table 5.

TABLE 5

| Component | 5A | 5B % w/v | 5C |
|---|---|---|---|
| Olopatadine HCl | 0.665 | 0.665 | 0.665 |
| Benzalkonium Chloride | 0.01 | 0.01 | 0.01 |
| Disodium EDTA | 0.01 | 0.01 | 0.01 |
| Sodium Chloride | 0.41 | 0.41 | 0.41 |
| Sodium Acetate | 0.5 | — | — |
| Sodium Borate | — | — | 0.5 |
| Sodium Citrate | — | 0.5 | — |
| Sodium Hydroxide | pH to 3.7 | pH to 3.7 | pH to 3.7 |
| Hydrochloric Acid[a] | pH to 3.7 | pH to 3.7 | pH to 3.7 |
| Purified Water | qs 100% | qs 100% | qs 100% |
| Batch Size | 100 mL | 100 mL | 100 mL |
| Sodium Hydroxide added | 0.332 g (1N) | 0.244 g (1N) | 0.963 g (1N) |
| Hydrochloric Acid added | 0.550 g (6N) | 0.550 g (6N) | 0.550 g (6N) |
| pH | 3.711 | 3.710 | 3.716 |
| Osmolality | 257 | 246 | 270 |
| Visual Observations: | | | |
| Observations: Initial | Upon addition of Olopatadine, batch appeared cloudy but began to clear within a few seconds | Upon addition of Olopatadine, batch appeared cloudy but began to clear within one minute | Upon addition of Olopatadine, batch appeared cloudy but began to clear with in a few seconds |
| Additional observations: | After 3 minutes of stirring, solution appeared clear with a few extraneous particles | After 17 minutes of stirring, solution appeared clear with several large flakey particles | After 16 minutes of stirring, solution appeared clear with a few large flakey particles |
| | After 20 additional minutes of stirring, solution appeared clear with very few extraneous particles | After 20 additional minutes of stirring, solution appeared clear with very few extraneous particles | After 20 additional minutes of stirring, solution appeared clear with very few extraneous particles |
| | The pH was adjusted, solution was brought to 100% of batch weight and remained clear (with very few extraneous particles) | The pH was adjusted, solution was brought to 100% of batch weight and remained clear (with very few extraneous particles) | The pH was adjusted, solution was brought to 100% of batch weight and remained clear (with very few extraneous particles) |

Example 9

Effect of Phosphate Buffer, NaCl, and Hot Water

The compositions shown in Table 6 were prepared to examine (1) the effect of adding phosphate buffer to a composition containing olopatadine hydrochloride, BAC, EDTA, NaOH/HCl, and NaCl, (2) the effect of adding NaCl to a composition containing olopatadine, BAC, EDTA, NaOH/HCl, and (3) the effect of hot water on the dissolution of olopatadine in a composition comprising olopatadine, BAC, EDTA, NaCl and NaOH/HCl. In each case, visual observations concerning the clarity of the composition were recorded. The results are shown in Table 6.

TABLE 6

| Component | 6A1 | 6A2 | 6B1 | 6B2 | 6C* |
|---|---|---|---|---|---|
| Olopatadine HCl | 0.665 (3) | Same | 0.665 (3) | Same | 0.665 (4) |
| Benzalkonium Chloride | 0.01 (5) | Same | 0.01 (2) | Same | 0.01 (3) |
| Disodium EDTA | 0.01 (4) | Same | 0.01 (1) | Same | 0.01 (2) |
| Sodium Chloride | 0.8 (1) | Same | — | Added 0.8% to existing solution | 0.8 (1) |
| Dibasic Sodium Phosphate | — | Added 0.5% to existing solution | — | — | — |

TABLE 6-continued

| Component | 6A1 | 6A2 | 6B1 | 6B2 | 6C* |
|---|---|---|---|---|---|
| Sodium Hydroxide | 2 drops added (2) qs pH to 3.7 (6) | Same | — | Same | pH to 3.7 |
| Purified Water | qs 100% | Same | qs 100% | Same | qs 100% |
| Batch Size | 50 mL | 25 mL | 50 mL | 25 mL | 50 mL |
| Initial pH | 3.329 | — | 2.838 | — | 2.873 |
| 1N NaOH added | 0.087 g | — | 0.343 g | — | 0.318 g |
| Final pH | 3.667 | — | 3.730 | — | 3.714 |
| Observations: | Upon addition of olopatadine HCl, solution appeared cloudy with many small white suspended particles | 25 mL portion of batch 1 - phosphate added and allowed to stir. Within 10 minutes, the solution appeared clear | Upon addition of olopatadine HCl, solution appeared cloudy with many small white suspended particles | 25 mL portion of batch 2 - NaCl added and allowed to stir. After 10 minutes of stirring, the solution remained clear | Upon addition of olopatadine HCl, the solution appeared cloudy with many white suspended particles |
| | After addition of EDTA and BAC, the solution appeared the same | After one day without stirring, solution appeared clear with a few extraneous fibers (7:30 am) | After 2 minutes of stirring, the solution began to clear, still with few many white particles | After one day without stirring, solution appeared clear with 2 small white flakey particles and a few extraneous fibers (7:30 am) | After 5 minutes of stirring, the solution began to clear, still with many small white suspended particles |
| | pH was adjusted to 3.7 and allowed to stir for 30 minutes, appearance was the same | Later that day (2:45 pm) batch was observed to be clear with many crystals formed at the bottom of the beaker | After 5 additional of stirring, the solution was clear | Later that day (2:45 pm) the batch appeared clear with very few (~3–4) small white flakey particles and a few extraneous fibers | After 20 minutes of stirring, the solution remained clear with many small white suspended particles |
| | After one day without stirring, the solution appeared clear with many small white particles at the bottom of the beaker (7:30 am) | Next day (8:00 am), batch remained the same | After pH adjust and qs to 100%, the batch remained clear | Next day (8:00 am), the batch remained the same | After 30 additional minutes of stirring, the solution remained the same |
| | Next day (8:00 am), batch remained the same. | | After one day without stirring, the solution remained clear (7:30 am) | | After pH adjust and qs to 100%, the solution was allowed to stir and appeared the same |
| | | | Next day (8:00 am) batch remained the same | | After one day without stirring, the solution appeared clear with many small white particles settled at the bottom of the beaker |

Note:
Number in parenthesis refers to order of addition of components.
*Hot purified water (~70° C.) was used.

Example 10

Buffer Capacity of Phosphate Buffer

Figure 5:
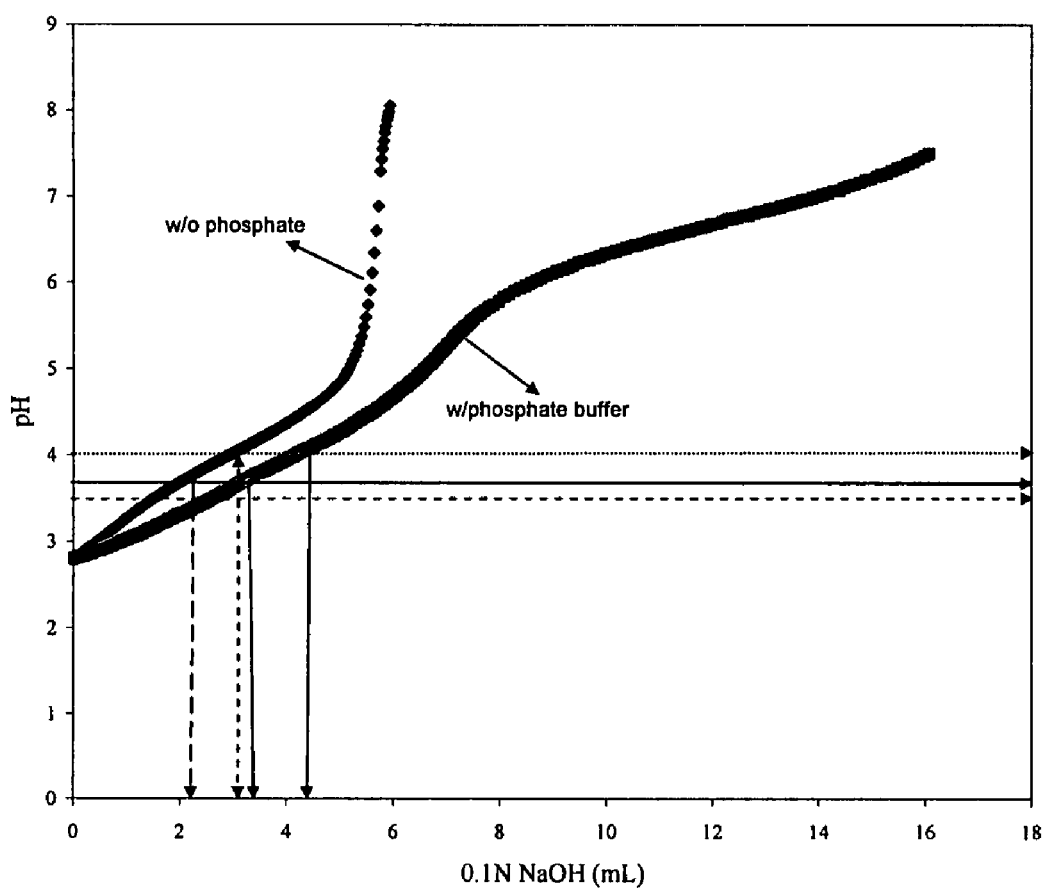
FIG. 5 shows the buffer capacity of an olopatadine nasal spray composition.

The contribution of phosphate buffer to the buffer capacity of the composition of Example 1 was determined in a classical acid-base titration experiment. The results are shown in FIG. 5. The buffer capacity of the composition of Example 1 (without phosphate buffer) was 2.66 from pH 3.5-3.8 and 2.7 from pH 3.5-3.9. The buffer capacity of the composition of Example 1 (i.e., including phosphate buffer) was 2.93 from pH 3.5-3.8 and 3.1 from pH 3.5-3.8.

Example 11

Stability of Olopatadine Nasal Spray Compositions Lacking Phosphate Buffer

The compositions (without phosphate buffer) shown below in Table 7A were prepared. Visual observations of the clarity of each composition were recorded as each composition was prepared. The results are shown in Table 7A.

TABLE 7A

| Component | 7A | 7B % w/v | 7C |
|---|---|---|---|
| Olopatadine HCl | 0.665 (2) | 0.665 (4) | 0.665 (5) |
| Benzalkonium Chloride | — | 0.01 (3) | 0.01 (4) |
| Disodium EDTA | — | 0.01 (2) | 0.01 (3) |
| Sodium Chloride | 0.8 (3) | 0.8 (5) | 0.8 (2) |
| Sodium Hydroxide | Adjust pH to 3.95 | Adjust pH to 3.95 | Adjust pH to 3.95 |
| Hydrochloric Acid | Adjust pH to 3.95 | Adjust pH to 3.95 | Adjust pH to 3.95 |
| Purified Water | qs 100% (1) | qs 100% (1) | qs 100% (1) |
| Batch Size | 200 ml | 200 mL | 200 mL |
| Osmolality | 286 | 286 | n/a |

TABLE 7A-continued

| Component | 7A | 7B<br>% w/v | 7C |
|---|---|---|---|
| Initial pH | 2.898 | 2.930 | 3.098 |
| Final pH | 3.947 | 3.952 | 3.957 |
| Observations: | Upon addition of drug, the solution appeared cloudy with many large flakey particles, after approx 20 minutes, the solution appeared clear with very few fibrous/small white particles (pH 2.845) Upon addition of NaCl, solution remained the same (pH 2.898) After pH adjust, final qs and several minutes of stirring, the final solution appeared clear with some fibrous particles and a few small white particles | Upon addition of drug, solution appeared cloudy with many large flakey particles; within approx 25 minutes, solution appeared clear with very few fibrous/small white particles (pH 2.880) Upon addition of NaCl, solution remained the same (pH 2.930) After pH adjust, final qs and several minutes of stirring, the final solution appeared clear with some fibrous particles and a few small white particles | Upon addition of drug, the solution appeared cloudy with many large flakey particles. After 3 hours of stirring the solution remained cloudy with many suspended particles After pH adjust and final qs, the solution remained cloudy with many suspended particles (while stirring) |

Note:
Numbers in parenthesis next to the components represents the order of addition.

Each of the compositions was then split. One portion of each was split again into three storage batches ("pre-filtration") and the other portion was filtered through a 0.2 μM filter and then split into three storage batches ("post-filtration"). One of the storage batches of each set was stored at room temperature (~22° C.), one in the refrigerator (~4° C.), and one subjected to freeze-thaw cycling (one day in the freezer (~−20° C.) and one day at room temperature, except over the weekends). Visual observations of the clarity of each sample of Formulation 7A (lacking BAC and EDTA) were recorded on the indicated days and the results were recorded. The results are shown in Tables 7B (pre-filtration) and 7C (post-filtration).

TABLE 7B

| | 7A Pre-Filtration | | |
|---|---|---|---|
| Observations: | Bottle 1 (at RT) | Bottle 2 (at 4° C.) | Bottle 3 (at FTC[a]) |
| Initial | Clear, many fibrous particles, a few small white particles | Clear, many fibrous particles, a few small white particles | Clear, many fibrous particles, a few small white particles |
| Day 1 | Clear, some fibrous particles, a few small white particles | Same | FT Cycle 1 - same |
| Day 2 | Same | Same | FT Cycle 2 - same |
| Day 5 | Clear, many fibrous particles, some small white particles | Same | FT Cycle 3 - same |
| Day 6 | Same | Same | FT Cycle 4 - same |
| Day 7 | Same | Same | FT Cycle 5 - same |
| Day 8 | Same | Same | FT Cycle 6 - Clear, many fibrous and small white particles |
| Day 9 | Same | Same | |
| Day 12 | Same | Clear, many fibrous and some small white particles, crystallization on bottom/sides of vial | |
| Day 13 | Same | Same | |
| Day 14 | Clear, many fibrous and small white particles (more than previous) | Same | |

A portion of the pre-filtered solution was transferred into three 20 mL glass vials and placed at the respective storage conditions for visual observation.
[a]Freeze-thaw cycle performed at 24 hour freeze/24 hour thaw except over weekends.

TABLE 7C

| | 7A Post-filtration | | |
|---|---|---|---|
| Observations | Bottle 1 (at RT) | Bottle 2 (at 4° C.) | Bottle 3 (at FTC[a]) |
| Initial | Clear, very few fibrous particles | Clear, very few fibrous particles | Clear, very few fibrous particles |
| Day 1 | Clear, a few fibrous particles, one small white particle | Same | FT Cycle 1 - Clear, few fibrous particles, few small white particles |
| Day 2 | Same | Clear, a few fibrous particles, some small white particles | FT Cycle 2 - Clear, few fibrous particles, very few small white particles |
| Day 5 | Clear, a few fibrous particles | Clear, a few fibrous particles, very few small white particles | FT Cycle 3 - same |
| Day 6 | Same | Same | FT Cycle 4 - same |
| Day 7 | Same | Same | FT Cycle 5 - same |
| Day 8 | Same | Same | FT Cycle 6 - same |
| Day 9 | Same | Same | |
| Day 12 | Same | Same | |
| Day 13 | Same | Same | |

TABLE 7C-continued

| | 7A Post-filtration | | |
|---|---|---|---|
| Observations | Bottle 1 (at RT) | Bottle 2 (at 4° C.) | Bottle 3 (at FTC[a]) |
| Day 14 | Same | Clear, a few fibrous and small white particles | |

Note:
A portion of the twice-filtered solution was transferred into three 50 mL media bottles and placed at the respective storage conditions for visual observation.
[a]Freeze-thaw cycle performed at 24 hour freeze/24 hour thaw except over weekends.

After nine days of observation, the post-filtration portion of Formulation 7A was split and a stir bar was added to each sample as a seeding agent (the stir bar was not rotating). Visual observations were recorded and the results are shown in Table 7 D.

TABLE 7D

| | 7A Post-filtration | | |
|---|---|---|---|
| Observations | Bottle 1 (at RT) | Bottle 3 (at 4° C.) | Bottle 5 (at FTC[a]) |
| | | With Stir Bar Added As a Seeding Agent | |
| Initial[b] | Clear, a few fibrous particles | Clear, a few fibrous particles | Clear, a few fibrous particles |
| Day 3 | Same | Clear, a few fibrous particles, very few small white particles | FT Cycle 1 - Clear, a few fibrous particles, very few small white particles |
| Day 4 | Same | Same | FT Cycle 2 - same |
| Day 5 | Same | Same | |

[a]Freeze-thaw cycle performed at 24 hour freeze/24 hour thaw except over weekends.
[b]Initial observations were performed prior to addition of stir bars.

To other portions of composition 7A split after nine days of observation, excess olopatadine (a few small granules) was added to both the pre-filtration and post-filtration samples to determine if seeding would cause olopatadine to precipitate. Visual observations were recorded on the indicated days. The results are shown in Tables 7 E (unfiltered composition) and 7 F (filtered composition).

TABLE 7E

| | 7A Pre-filtration (with excess olopatadine HCl) | |
|---|---|---|
| Observations | Bottle 1 (at RT) | Bottle 2 (at FTC[a]) |
| Initial[b] | Clear, many fibrous particles, some small white particles | Clear, many fibrous particles, some small white particles |
| Day 3 | Clear, many fibrous/small white particles (powdery settling) | FT Cycle 1 - clear, many fibrous/small white particles (powdery settling) |
| Day 4 | Same | FT Cycle 2 - same |
| Day 5 | Same | |

[a]Freeze-thaw cycle performed at 24 hour freeze/24 hour thaw except over weekends.
[b]Initial observations were performed prior to addition of excess olopatadine HCl.

TABLE 7F

| | 7A Post-filtration | | |
|---|---|---|---|
| Observations | Bottle 2 (at RT) | Bottle 4 (at 4° C.) | Bottle 6 (at FTC[a]) |
| | | With Excess Olopatadine HCl Added (1–2 small granules) | |
| Initial[b] | Clear, a few fibrous particles | Clear, a few fibrous particles | Clear, a few fibrous particles |
| Day 3 | Clear, many fibrous and small white particles | Clear, many fibrous and small white particles (powdery at bottom of vial, settling) | FT Cycle 1 - Clear, many fibrous/small white particles (powdery at bottom of vial, settling) |
| Day 4 | Same | Same | FT Cycle 2 - same |
| Day 5 | Same | Same | |

A portion of the solutions that had been through nine days of observations at RT and 4° C. and four FT cycles were transferred into three 20 mL glass vials and spiked with olopatadine HCl. These units were then placed at the respective storage conditions for visual observation.
[a]Freeze-thaw cycle performed at 24 hour freeze/24 hour thaw except over weekends.
[b]Initial observations were performed prior to addition of excess olopatadine HCl.

The stability of the composition "7B" (containing BAC and EDTA) was evaluated in the same fashion. The results are shown in Tables 7G (Pre-filtration), 7H (Post-filtration), 7I (with stir bar added after 9 days), 7J (with excess olopatadine added after 9 days; pre-filtration), and 7K (with excess olopatadine added after 9 days; post-filtration).

TABLE 7G

| | 7B Pre-filtration | | |
|---|---|---|---|
| Observations: | Bottle 1 (at RT) | Bottle 2 (at 4° C.) | Bottle 3 (at FTC[a]) |
| Initial | Clear, many fibrous particles, a few small white particles | Clear, many fibrous particles, a few small white particles | Clear, many fibrous particles, a few small white particles |
| Day 1 | Clear, some fibrous particles, small white particles | Same | FT Cycle 1 - Same |
| Day 2 | Same | Same | FT Cycle 2 - Same |
| Day 5 | Clear, many fibrous particles, some small white particles | Same | FT Cycle 3 - Same |
| Day 6 | Same | Same | FT Cycle 4 - same |
| Day 7 | Same | Same | FT Cycle 5 - same |
| Day 8 | Same | Same | FT Cycle 6 - Clear, many fibrous and small white particles |
| Day 9 | Same | Same | |
| Day 12 | Same | Same | |
| Day 13 | Same | Same | |
| Day 14 | Clear, many fibrous and small white particles (more than previous) | Same | |

A portion of the pre-filtered solution was transferred into three 20 mL glass vials and placed at the respective storage conditions for visual observation.
[a]Freeze-thaw cycle performed at 24 hour freeze/24 hour thaw except over weekends.

TABLE 7H

| | 7B Post-filtration | | |
|---|---|---|---|
| Observations | Bottle 1 (at RT) | Bottle 2 (at 4° C.) | Bottle 3 (at FTC[a]) |
| Initial | Clear, very few fibrous particles | Clear, very few fibrous particles | Clear, very few fibrous particles |
| Day 1 | Clear, a few fibrous particles | Same | FT Cycle 1 - Clear, few fibrous particles, few small white particles |
| Day 2 | Same | Clear, a few fibrous particles, some small white particles | FT Cycle 2 - Clear, few fibrous particles, very few small white particles |
| Day 5 | Same | Clear, a few fibrous particles, very few small white particles | FT Cycle 3 - same |
| Day 6 | Same | Same | FT Cycle 4 - same |
| Day 7 | Same | Same | FT Cycle 5 - same |
| Day 8 | Same | Same | FT Cycle 6 - same |
| Day 9 | Same | Same | |
| Day 12 | Same | Clear, a few fibrous and small white particles (more than previous) | |
| Day 13 | Same | Clear, a few fibrous/small white particles, light layer of crystallization forming on bottom/sides of bottle | |
| Day 14 | Same | Same | |

Note:
A portion of the twice-filtered solution was transferred into three 50 mL media bottles and placed at the respective storage conditions for visual observation.
[a]Freeze-thaw cycle performed at 24 hour freeze/24 hour thaw except over weekends.

TABLE 7I

| | 7B Post-filtration | | |
|---|---|---|---|
| Observations | Bottle 7 (at RT) | Bottle 9 (at 4° C.) With Stir Bar Added | Bottle 11 (at FTC[a]) |
| Initial[b] | Clear, a few fibrous particles | Clear, a few fibrous particles | Clear, a few fibrous particles |
| Day 3 | Clear, a few fibrous particles, very few small white particles | Clear, a few fibrous and small white particles | FT Cycle 1 - Clear, a few fibrous particles, very few small white particles |
| Day 4 | Same | Clear, a few fibrous/small white particles, powdery at bottom of vial, settling | FT Cycle 2 - Clear, a few fibrous and small white particles |
| Day 5 | Same | Clear, settling on bottom, many very fine white particles | |

Note:
A portion of the solutions that had been through nine days of observations at RT and 4° C. and four FT cycles were transferred into three 20 mL glass vials with stir bars added and placed at the respective storage conditions for visual observation.
[a]Freeze-thaw cycle performed at 24 hour freeze/24 hour thaw except over weekends.
[b]Initial observations were performed prior to addition of stir bars.

TABLE 7J

| Obser-vations | 7B Pre-filtration (with excess olopatadine HCl) | |
|---|---|---|
| | Bottle 3 (at RT) | Bottle 4 (at FTC[a]) |
| Initial[b] | Clear, many fibrous particles, some small white particles | Clear, many fibrous particles, some small white particles |
| Day 3 | Clear, many fibrous/small white particles (light powdery settling) | FT Cycle 1 - clear, many fibrous/small white particles (powdery settling) |
| Day 4 | Same | FT Cycle 2 - same |
| Day 5 | Same | |

A portion of the pre-filtered solutions that had been through nine days of observations at RT and 4° C. and four FT cycles were transferred into three 20 mL glass vials and spiked with olopatadine HCl. The units were then placed at the respective storage conditions for visual observation.
[a]Freeze-thaw cycle performed at 24 hour freeze/24 hour thaw except over weekends.
[b]Initial observations were performed prior to addition of excess olopatadine HCl.

TABLE 7K

7B Post-filtration

| Observations | Bottle 8 (at RT) | Bottle 10 (at 4° C.) With Excess Olopatadine Added (1–2 small granules) | Bottle 12 (at FTC[a]) |
|---|---|---|---|
| Initial[b] | Clear, a few fibrous particles | Clear, a few fibrous particles | Clear, a few fibrous particles |
| Day 3 | Clear, many fibrous and small white particles | Clear, many fibrous and small white particles (powdery at bottom of vial, settling) | FT Cycle 1 - Clear, many fibrous/small white particles (powdery at bottom of vial, settling) |
| Day 4 | Same | Clear, many fibrous/small white particles, crystallization at bottom of vial | FT Cycle 2 - same |
| Day 5 | Same | Same | |

A portion of the solutions that had been through nine days of observations at RT and 4° C. and four FT cycles were transferred into three 20 mL glass vials and spiked with olopatadine HCl. These units were then placed at the respective storage conditions for visual observation.
[a]Freeze-thaw cycle performed at 24 hour freeze/24 hour thaw except over weekends.
[b]Initial observations were performed prior to addition of excess olopatadine HCl.

Example 12

Effect of Phosphate Buffer

The compositions shown below in Table 8 were prepared using a compounding procedure similar to that described in Example 1. In all four cases, the NaCl was added after olopatadine during the compounding. All four compositions contained the equivalent of 110% of a 0.6% targeted concentration. Two of the compositions were formulated at a pH of 3.95 and two at 4.10 to test an extreme condition. The results are shown in Table 8.

TABLE 8

| | Formulation 12A % (w/v) | Formulation 12B % (w/v) | Formulation 12C % (w/v) | Formulation 12D % (w/v) |
|---|---|---|---|---|
| Olopatadine HCl | 0.732 | 0.732 | 0.732 | 0.732 |
| Benzalkonium Chloride | 0.01 | 0.01 | 0.01 | 0.01 |
| Disodium EDTA | 0.01 | 0.01 | 0.01 | 0.01 |
| Sodium Chloride | 0.41 | 0.41 | 0.8 | 0.8 |
| Dibasic Sodium Phosphate, Anhydrous | 0.5 | 0.5 | — | — |
| Sodium Hydroxide | pH to 3.95 | pH to 4.10 | pH to 3.95 | pH to 4.10 |
| Hydrochloric Acid | pH to 3.95 | pH to 4.10 | pH to 3.95 | pH to 4.10 |
| Purified Water | qs 100% | qs 100% | qs 100% | qs 100% |
| Visual Observations: | | | | |
| Initial | Clear solution | Clear solution | Clear solution | Clear solution |
| Room Temperature (4 days) | Remained clear | Remained clear | Remained clear | Remained clear |
| 4° C. (4 days) | Remained clear on days 1, 2, 3 and 4. No precipitate was found. | Remained clear on days 1, 2, and 3. On day 4, a very small amount of clear crystals formed at the bottom of the glass vial. | Remained clear on days 1, 2, 3, and 4. No precipitate was found. | Remained clear on days 1, 2, and 3. On day 4, a significant amount of clear crystals formed at the bottom of the glass vial. |

Comparing the results of Formulations B and D demonstrates that compositions with phosphate buffer are more stable against crystal formation than compositions without phosphate buffer.

Example 13

Storage Stability

The solution stability of the composition of Example 1 was examined by preparing variations of the composition at the pH's shown in Table 9 and subjecting the samples to 13 freeze-thaw cycles (same cycles as described in Example 11 above). Following the last cycle, the samples were stored in the freezer for approximately three weeks and then analyzed. The amount of olopatadine (pre- and post-filtration, 0.2 μM filter) was determined by HPLC assay as a percent of the labeled amount (0.6%). The samples were evaluated using four tests of solution clarity: "Nephelos" values were obtained using a turbidimeter (HF Scientific, Inc., Model No. DRT100B); "Clarity" was determined by visual observation using a method similar to the Ph. Eur. (5$^{th}$ Edition) method for evaluating solution clarity and degree of opalescence; "Precipitate" was determined by visual inspection and the presence of absence of precipitates was recorded; "Particles by Visual Observation" was determined by visual inspection under a light box where not more than 3 particles per 5 mL sample is considered "essentially particle free." Osmolality and pH were also determined for each composition. The results are shown in Table 9. In four of the five cases (Samples 1-4), the compositions were clear solutions following the freeze-thaw cycling study, demonstrating the composition of Example 1 is a stable aqueous solution despite the absence of a polymeric physical stability-enhancing agent. The sample that did not remain a clear solution is Sample 5 (pH=4.45).

TABLE 9

| Sample Lot | Olopatadine Assay (% of label) | | Pre filtration Physical Test Results | | | | | |
|---|---|---|---|---|---|---|---|---|
| | Pre-Filtration | Post-Filtration | Nephelos[1] (In NTU) | Clarity | Precipitate | Particles by Visual Observation | Osmolality mOsm/Kg | pH |
| 1 | 99 99 | 100 99 | 0.3 | Clear, NMT EP1 | None | Essentially particle-free | 280 | 3.83 |
| 2 | 99 97 | 100 99 | 0.2 | Clear, NMT EP1 | None | Essentially particle-free | 288 | 3.94 |
| 3 | 100 98 | 101 99 | 0.2 | Clear, NMT EP1 | None | Essentially particle-free | 285 | 4.01 |
| 4 | 98, 99, | 98 99 | 0.5 | Clear, NMT EP1 | None | Essentially particle-free | 287 | 4.15 |
| 5 | 98 98 | 98 98 | (a) Crystal Form In one Test Tube (b) Other test tube clear (0.6, 0.5)[2] | Clear, NMT EP1 | None | Essentially particle-free | 294 | 4.45 |

[1]Nephelos (Turbidity) of ≦3 NTU is considered clear solution as per Ph. Eur. (5$^{th}$ Ed.)
[2]Pre and post olopatadine assay, nephalos, clarity, precipitate, particles by visual observation, osmolality and pH were performed using clear solution from second test tube.

This invention has been described by reference to certain preferred embodiments; however, it should be understood that it may be embodied in other specific forms or variations thereof without departing from its special or essential characteristics. The embodiments described above are therefore considered to be illustrative in all respects and not restrictive, the scope of the invention being indicated by the appended claims rather than by the foregoing description.

What is claimed is:

1. A topically administrable, aqueous, nasal spray solution composition consisting of
   a) 0.665% (w/v) olopatadine hydrochloride;
   b) a phosphate salt in an amount equivalent to 0.4-0.6% (w/v) dibasic sodium phosphate, wherein the phosphate salt selected from the group consisting of monobasic sodium phosphate; dibasic sodium phosphate; tribasic sodium phosphate; monobasic potassium phosphate; dibasic potassium phosphate; and tribasic potassium phosphate;
   c) 0.35-0.45% (w/v) NaCl;
   d) one or more pH-adjusting agents in an amount sufficient to cause the composition to have a pH of 3.6-3.8, wherein the pH-adjusting agents are selected from the group consisting of HCl and NaOH;
   e) 0.005-0.015% (w/v) benzalkonium chloride;
   f) 0.005-0.015% (w/v) edetate disodium; and
   g) water;
   wherein the composition has an osmolality of 260-330 mOsm/kg.

2. A topically administrable, aqueous, nasal spray solution composition consisting of
   a) 0.665% (w/v) olopatadine hydrochloride;
   b) 0.4-0.6% (w/v) dibasic sodium phosphate;
   c) 0.35-0.45% (w/v) NaCl;
   d) one or more pH-adjusting agents in an amount sufficient to cause the composition to have a pH of 3.6-3.8, wherein the pH-adjusting agents are selected from the group consisting of HCl and NaOH;
   e) 0.01% (w/v) benzalkonium chloride;
   f) 0.01% (w/v) edetate disodium; and
   g) water;
   wherein the composition has an osmolality of 260-330 mOsm/kg.

* * * * *